(12) United States Patent
Baranowitz (10) Patent No.: US 6,878,747 B2
(45) Date of Patent: Apr. 12, 2005

(54) SYSTEMIC FORMULATIONS CONTAINING BETA-CAROTENE AND DERIVATIVES THEREOF

(76) Inventor: Steven A. Baranowitz, Cedarbrook Hill Apts., 8470 Limekiln Pike - Bldg. 2, Apt. 519, Wyncote, PA (US) 19095

(*) Notice: Subject to any disclaimer, the term of this patent is extended or adjusted under 35 U.S.C. 154(b) by 0 days.

(21) Appl. No.: 10/466,825

(22) PCT Filed: Jan. 28, 2002

(86) PCT No.: PCT/US02/02465

§ 371 (c)(1),
(2), (4) Date: Aug. 21, 2003

(87) PCT Pub. No.: WO02/058586

PCT Pub. Date: Aug. 1, 2002

(65) Prior Publication Data

US 2004/0068009 A1 Apr. 8, 2004

Related U.S. Application Data (60) Provisional application No. 60/264,443, filed on Jan. 26, 2001.

(51) Int. Cl.[7] .......................... A61K 31/19; A61K 31/11; A61K 31/07
(52) U.S. Cl. .......................... 514/557; 514/703; 514/725
(58) Field of Search .............................. 514/557, 703, 514/725

(56) References Cited

U.S. PATENT DOCUMENTS

| | | | | |
|---|---|---|---|---|
| 5,055,446 A | * | 10/1991 | Alexander et al. | 514/2 |
| 5,260,279 A | * | 11/1993 | Greenberg | 514/21 |
| 5,658,949 A | * | 8/1997 | Aggarwal | 514/557 |
| 5,891,470 A | * | 4/1999 | Rinaldi et al. | 424/451 |
| 6,264,986 B1 | * | 7/2001 | Hahnlein et al. | 424/489 |
| 6,426,078 B1 | * | 7/2002 | Bauer et al. | 424/401 |

FOREIGN PATENT DOCUMENTS

| | | | |
|---|---|---|---|
| WO | WO 98/16204 | * | 4/1998 |

OTHER PUBLICATIONS

HCAPLUS Abstract, AN 1993:595198 Cooney et al., Methodsin Enzymology (1993), 214 (Carotenoids, Pt. B), 55–68.*

Database HCAPLUS on ACS No. 2000:419783, Kim et al. Controlled Release of All–Trans–Retinoic Acid from PEGylated Gelatin Nanoparticles By Enzymatic Degradation. Abstract, 1999, 4 (3), pp. 215–218.

Database HCAPLUS on ACS No. 1998:253034, Bausch et al. Process for the Manufacture of A Powderey Preparation. WO 9816204A1 Apr. 23, 1998.

Database HCAPLUS on ACS No. 1993:595198, Cooney et al. Solubilization, Cellular Uptake, and Activity of Beta–Carotene and Other Carotenoids as Inhibitors of Neoplastic Transformation in Cultured Cells. Method Enzymol. 1993, vol. 214, pp. 55–68.

* cited by examiner

Primary Examiner—Raymond J. Henley, III
(74) Attorney, Agent, or Firm—Darby & Darby (57) ABSTRACT

Disclosed herein are systemic formulations comprising beta-carotene and a solubilizer selected from tetrahydrofuran (THF), polyethylene glycol (PEG), and mixtures thereof. Generally, the formulations are administered to animals in need thereof in therapeutically effective amounts of beta-carotene for the purpose intended. The solubilizers greatly enhance the bioavailability of beta-carotene administered systemically. Another embodiment of the present invention is a method for administering beta-carotene to an animal in need thereof by administering the formulation of the present invention. Yet another embodiment is a method for treating an animal in need thereof by administering a therapeutically effective amount of the formulation of the present invention. The invention includes a method for treating an animal suffering from or susceptible to sepsis by administering an effective amount for treating sepsis of the formulation of the present invention.

34 Claims, 5 Drawing Sheets

SYSTEMIC FORMULATIONS CONTAINING BETA-CAROTENE AND DERIVATIVES THEREOF

This application is a U.S. national phase application under 35 U.S.C. §371 of International Patent Application No. PCT/US02/02465 filed Jan. 28, 2002 and claims the benefit of U.S. Provisional Application Ser. No. 60/264,443, entitled "SYSTEMIC FORMULATIONS CONTAINING BETA-CAROTENE AND DERIVATIVES THEREOF," filed Jan. 26, 2001, and which is hereby incorporated by reference in its entirety. The International Application was published in English on Aug. 1, 2002 as WO 02/058586 A2 under PCT Article 21(2).

FIELD OF THE INVENTION

The present invention relates to a systemic formulation containing beta-carotene and derivatives thereof and a solubilizer, such as tetrahydrofuran or polyethylene glycol, and methods of administering beta-carotene and derivatives thereof by administering the systemic formulation. The invention also relates to a method of treating an animal suffering from or susceptible to sepsis by administering beta-carotene and derivatives thereof.

BACKGROUND OF THE INVENTION

For decades, beta-carotene, a carotenoid present in many green and yellow vegetables, was used to treat beta-carotene and vitamin A deficiencies in mammals. Recently, beta-carotene has been reported to have many important biological functions in addition to its role as a vitamin A precursor. For example, beta-carotene has been shown to have broad anti-cancer (Krinsky, 1990Iftikhar et al. 1996) and anti-toxic effects (Martin et al. 1996Baranowitz & Maderson, 1993, 1995,1997). More specifically, it has been reported to protect mammalian cells against cytotoxicity and genotoxicity in both in vivo and in vitro experimental model systems (Krinsky et al., 1993).

Various epidemiological studies have also suggested that high beta-carotene intake may reduce the incidence of a number of life-threatening diseases, such as cancer (Krinsky, N. I. et al. eds., 1989 in Carotenoids Chemistry and Biology, Plenham Press, New York). Beta-carotene has also been reported to effectively treat the most common cause of blindness in the U.S., age-related macular degeneration (Baranowitz & Brookner, 1994, 1995). The protective effects of beta-carotene may be attributed to the ability of beta-carotene to quench a variety of free radical species (Foote et al., 1970).

A major drawback of the use of beta-carotene for the treatment of various diseases is that the beta-carotene molecule is highly lipophilic and therefore poorly taken up by most animals (Wamer et al., (1985) Nutr. Rep. Int., 32, 295–301) and cell-lines in culture (Renner et al., (1985) Mutat. Res. 144, 251–256). In order to optimize delivery of beta-carotene, researchers have investigated a variety of drug delivery vehicles in an attempt to increase beta-carotene's bioavailibility in animal tissues but have had little success. Dimethylsulfoxide, for instance, was not found to be a suitable vehicle for incorporating high carotenoid concentrations (Craft, 1992; Gross et al. 1997).

Therefore, there is a need for a method for administering high concentrations of beta-carotene with low toxicity and high tolerability. Such a method would preferably be simple to administer and use relatively inexpensive materials.

SUMMARY OF THE INVENTION

It has now been discovered that certain solubilizers greatly enhance the bioavailability of beta-carotene and derivatives thereof administered systemically. More specifically, it has been discovered that the bioavailability of beta-carotene and derivatives thereof systemically administered is surprisingly increased by solubilizing the beta-carotene in tetrahydrofuran, polyethylene glycol, and mixtures thereof prior to administration. Furthermore, beta-carotene and derivatives thereof solubilized in tetrahydrofuran, polyethylene glycol, and mixtures thereof delivers beta-carotene and derivatives thereof faster to target sites than similar formulations without the solubilizer.

In one aspect, the present invention provides a systemic formulation comprising beta-carotene and derivatives thereof and a solubilizer selected from tetrahydrofuran (THF), polyethylene glycol (PEG), and mixtures thereof.

Another aspect of the present invention is directed to a method for administering beta-carotene and derivatives thereof to an animal in need thereof by administering the formulations of the present invention.

Yet another aspect of the present invention is directed to a method for treating an animal in need thereof by administering a therapeutically effective amount of the formulations of the present invention.

It has also been discovered that beta-carotene and derivatives thereof are effective at treating sepsis. A still further aspect of the present invention, thus, is directed to a method for treating an animal suffering from or susceptible to sepsis by administering an effective amount of beta-carotene and derivatives thereof to the animal. According to a preferred embodiment, the animal is administered an effective amount of the formulation of the present invention.

These and other aspects of the present invention will be apparent to those of ordinary skill in the art in light of the present specifications, claims and drawings.

DETAILED DESCRIPTION OF THE INVENTION

"Derivatives"—of beta-carotene are defined herein as retinol, retinoic acid, 9-cis retinoic acid, retinal and retinyl.

In the discussions below, it should be understood that the term "beta-carotene" will mean "beta-carotene and derivatives thereof" whether or not explicitly stated.

It has now been discovered that the bioavailabllity of beta-carotene and derivatives thereof systemically administered is surprisingly increased by solubilizing the beta-carotene in tetrahydrofuran (THF), polyethylene glycol (PEG), and mixtures thereof prior to administration. Furthermore, beta-carotene and derivatives thereof solubilized in tetrahydrofuran, polyethylene glycol, and mixtures thereof delivers beta-carotene and derivatives thereof faster to target sites than similar formulations without the solubilizer.

The invention includes a systemic formulation comprising beta-carotene and derivatives thereof and a solubilizer selected from THF, PEG, or a mixture thereof for use in methods to treat animals. The methods involve administering thereof therapeutically effective amounts of beta-carotene and derivatives thereof for the purpose intended.

THF for use in the present invention is commercially available from Sigma Chemical Co., St. Louis, Mo. or Fisher Scientific Co., Pittsburg, Pa.

Suitable polyethylene glycols include, but are not limited to, those having a molecular weight ranging from about 200 to about 600 daltons. A preferred polyethylene glycol is PEG 200. PEG for use in the present invention is commercially available from numerous sources such as Sigma Chemical Co. or Fisher Scientific Co.

The formulation broadly comprises from about 0.1 to about 9.3 mg and preferably from about 1 to about 6 mg of beta-carotene per ml of tetrahydrofuran. The maximum concentration of beta-carotene capable of dissolving in THF is 9.3 mg/ml. Solubility problems arise above this concentration of beta-carotene. Beta-carotene and derivatives thereof for use in the present invention is commercially available from Sigma Chemical Co. or Fisher Scientific Co.

The formulation broadly comprises from about 0.1 to about 1 mg and preferably from about 0.3 to about 0.5 mg of beta-carotene per ml of polyethylene glycol.

According to a preferred embodiment, the formulation contains both tetrahydrofuran and polyethylene glycol. The weight ratio of tetrahydrofuran to polyethylene glycol generally ranges from about 90:10 to about 99.5:0.5 and preferably ranges from about 95:5 to about 99:1. For example, the weight ratio may be about 97:3.

The formulations of the present invention do not have to contain a therapeutically effective amount of beta-carotene and derivatives thereof for the intended purpose, i.e., an amount sufficient to reduce or prevent a disease or other ailment, because such effective amounts can be attained by administering a plurality of such formulations. Since the formulations of the present invention exhibit greater delivery of beta-carotene and derivatives thereof than prior art formulations, less beta-carotene may be administered in order to achieve the same effect as with prior art formulations.

The formulation may be a liquid, solid, or gel. Liquid formulations may also include additives, such as excipients, stabilizers, buffers, diluents, suspending agents, preservatives, colorants, dosing vehicles, or any combination of any of the foregoing. Typically, these additives are pharmaceutically acceptable additives, such as those described in Remington's, The Science and Practice of Pharmacy, (Gennaro, A. R., ed., 19$^{th}$ edition, 1995, Mack Pub. Co.) which is herein incorporated by reference. The phrase "pharmaceutically acceptable" refers to additives or compositions that are physiologically tolerable and do not typically produce an allergic or similar untoward reaction, such as gastric upset, dizziness and the like, when administered to a mammal.

Suitable suspending agents include, but are not limited to, cellulose ethers, such as carboxymethyl cellulose, olive oil, corn oil and saline (Sigma Chemical Co., Fisher Scientific Co.). Generally, the formulation includes from about 0.1 to about 20% by weight of suspending agent, based upon 100% total weight of the formulation.

Suitable preservatives include, but are not limited to, preservatives known in the art of pharmaceuticals such as butylated hydroxytoluene (BHT) (Sigma Chemical Co., Fisher Scientific Co.) Generally, the formulation includes from about 0.01 to about 1% by weight of preservative, based upon 100% total weight of formulation.

The formulation may include any dosing vehicle known in the art. Preferred dosing vehicles include, but are not limited to those which are used in formulations intended for administration to mammals especially humans such as, sterile liquids, e.g., USP water and oils. Suitable oils include, but are not limited to, petroleum oil, animal oil, vegetable oil, and synthetic oils. Non-limiting examples of suitable oils include corn oil, peanut oil, soybean oil, mineral oil, and sesame oil (Sigma Chemical Co., St. Louis, Mo.; Fisher Scientific, Pittsburgh, Pa.). Water, aqueous saline solutions, aqueous dextrose solutions, and aqueous glycerol solutions are preferred dosing vehicles, particularly for injectable solutions. Generally, the formulation includes from about 5 to about 95% by weight of dosing vehicle, based upon 100% total weight of formulation.

Liquid formulations of the present invention may be sterile and non-sterile injectable formulations. For instance, the formulation may be an aqueous or oleaginous suspension. The suspensions may be formulated according to techniques known in the art using suitable dispersing or wetting agents and suspending agents. The injectable formulation may also be a sterile injectable solution or suspension in a non-toxic parenterally-acceptable diluent or solvent. Suitable diluents and solvents for injectable formulations include 1,3-butanediol, water, Ringer's solution and isotonic sodium chloride solution. Sterile, fixed oils are conventionally employed as a solvent or suspending medium. Suitable fixed oils include, but are not limited to, synthetic mono- or di-glycerides; fatty acids, such as oleic acid and its glyceride derivatives; and natural pharmaceutically-acceptable oils, such as olive oil, castor oil, and polyoxyethylated derivatives thereof. (Sigma Chemical Co.; Fisher Scientific) According to a preferred embodiment, oil containing injectable formulations contain a long-chain alcohol diluent.

Topical formulations of the present invention are typically in the form of an ointment (or suspension). Such formulations may be administered for diseases of the eye, the skin, and the lower intestinal tract. Suitable suspending agents, diluents, and dosing vehicles for such formulations include, but are not limited to, mineral oil, liquid petrolatum, white petrolatum, propylene glycol, polyoxyethylene, polyoxypropylene compound, emulsifying wax and water. (Sigma Chemical Co.; Fisher Scientific) Alternatively, the topical formulation can be in the form of a lotion or cream. Suitable suspending agents, diluents, and dosing vehicles for such formulations include, but are not limited to, mineral oil, sorbitan monostearate, polysorbate 60 cetyl esters wax, cetearyl alcohol, 2-octyldodecanol, benzyl alcohol and water. (Sigma Chemical Co.; Fisher Scientific) Topical application for the lower intestinal tract can be effected in a rectal suppository formulation or in a suitable enema formulation. The formulation may also be administered via a transdermal patch as known in the art.

The liquid formulation may also be applied ophthalmically. A preferred ophthalmic formulations of the present invention is a micronized suspension in isotonic, pH adjusted sterile saline. A preservative, such as benzalkonium chloride, may be included in the formulation. Alternatively, the ophthalmic formulation is in an ointment, for example, containing petrolatum.

Nasal aerosol and inhalation formulations of the invention may be prepared by any method in the art. Such formulations may include dosing vehicles, such as saline; preservatives, such as benzyl alcohol; absorption promoters to enhance bioavailability; fluorocarbons used in the delivery systems, e.g., nebulizers, etc.; solubilizing agents; dispersing agents; or any combination of any of the foregoing.

Typical additives for solid formulations include, but are not limited to, excipients, diluents, stabilizers, disintegrants, lubricants, plasticizers, colorants, preservatives, dosing vehicles, and any combination of any of the foregoing. Preferably, these additives are pharmaceutically acceptable additives. The solid formulations may be in the form of capsules or tablets. Typically, tablets include a carrier, such as lactose and corn starch, and a lubricating agent, such as magnesium stearate. Capsules typically include a diluent, such as lactose and dried corn starch.

The formulations of the present invention may be administered systemically. The term "systemic" as used herein includes parenteral, topical, oral, spray inhalation, rectal, nasal, bucal, and vaginal administration. The term "parenteral" as used herein includes subcutaneous, intravenous, intramuscular, intra-articular, intra-synovial, intrasternal, intrathecal, intrahepatic, intralesional and intracranial administration. Preferably, the compositions are administered orally, intraperitoneally or intravenously.

The formulations of the present invention can be administered to animals, such as vertebrates, (especially mammals) including, but not limited to, fowl (e.g., chickens), cows, horses, sheep, pigs, goats, cats, dogs, hamsters, mice, rats, monkeys, rabbits, chimpanzees, and humans. In a preferred embodiment, the subject is a human.

Typically, a therapeutically effective amount of the formulation is administered to treat an animal in need thereof. Preferably, an effective amount of the formulation is administered to treat an animal suffering from or susceptible to a disease for which beta-carotene and derivatives thereof is effective. For example, an effective amount of the formulations of the present invention may be administered to treat age-related macular degeneration and melanoma would range between about 0.01 and about 20 mg/kg body weight of the recipient. The formulations of the present invention can be used in the methods to transdifferentiate cells and tissues and replace lost body parts described in PCT/US/00/21015. In addition, at least 250 mg/day is administered to individuals having abnormal immunological and serological indices as disclosed in U.S. Pat. No. 6,251,953, issued Jun. 26, 2001.

The amount of beta-carotene and derivatives thereof may vary depending on the disease or ailment to be treated. For example, about 300 mg of beta-carotene and derivatives thereof is orally administered to a human per day (or, for a 75 kg human, up to about 4 mg per kg per day). Preferably, from about 200 to about 500 mg of beta-carotene and derivatives thereof is administered per day.

The present inventor has also discovered that beta-carotene and derivatives thereof is effective at treating sepsis. The invention, thus, includes a method for treating an animal suffering from or at risk for developing sepsis by administering an effective amount of the formulation of the present invention containing beta-carotene and derivatives thereof to the animal. For humans, broadly from about 1 to about 20 mg per kg body weight of the recipient of beta-carotene and from about 0.1 to about 2 mg for a body weight of the recipient for the derivatives and preferably from about 4 to about 9 mg per kg body weight of the recipient of beta-carotene and from about 0.4 to about 0.9 mg per kg body weight of the recipient for the derivatives is administered per day. According to a preferred embodiment, the animal is administered an effective amount for treating sepsis of the formulation of the present invention.

In this context, "treatment" is defined herein as administration to individuals suffering from sepsis or prophylactic administration to those at risk for developing sepsis, e.g., those who have undergone or about to undergo surgery.

Demetriou, A. A. et al. (Arch. Surg. 119: 167–165 1984) compared the effects of Vitamin A and beta-carotene on intra-abdominal sepsis in a rat model for the disease. Whereas supplementation with Vitamin A had a significant protective effect, dietary supplementation with beta-carotene (90 mg /kg) had a lesser effect. The authors concluded that supplemental beta-carotene did not appear to be as effective as supplemental Vitamin A and stated ". . . this may be due to slower absorption of beta-carotene from the G.I. tract . . . and/or possible slow conversion of beta-carotene to Vitamin A in these animals . . . ". It is expected that the use of compositions of the present invention will overcome these deficiencies.

The invention is further described below in working examples, which are intended to illustrate the present invention without limiting the scope thereof.

EXAMPLE 1

The solutions described in Table 1 were prepared by mixing the appropriate ingredients. The beta-carotene (synthetic beta-carotene (type I)), butylated hydroxytoluene (BHT), polyethylene glycol 200 (PEG 200), and corn oil are available from Sigma of St. Louis, Mo. The 0.9% normal saline solution is available from Abbott Laboratories of North Chicago, Ill.

TABLE 1

| Solution | Ingredients |
|---|---|
| A | 9 mg beta-carotene per ml THF |
| B | 1 mg beta-carotene per ml PEG 200 |
| C | 9 mg beta-carotene per ml vehicle (where the vehicle is 97% (w/w) THF with 3% (w/w) PEG 200) |
| D | 0.9% normal saline solution |
| E | 50% (w/w) Formulation A dispersed in 50% (w/w) corn oil |

EXAMPLE 2

10 week old Mongolian gerbils (obtained from Charles River Laboratories of Newfeld, N.J.) were injected intraperitoneally (IP) with solutions A–E of Example 1 at the dosages indicated in Table 2 below to determine their toxicity. Solutions A, C, and E were injected with glass syringes while solutions B and D were injected with plastic syringes. The gerbils were then observed for up to 7 days. The results are shown in Table 2.

TABLE 2

| Solution | Dose (ml) | Weight of Gerbil (g) | Equivalent Dosage of β-carotene (mg/kg) | Toxicity (Activity of Gerbil) | Route of Administration |
|---|---|---|---|---|---|
| A | 0.01 | 49 | 1.8 | Normally active after the injection, and 1 and 7 days later. | IP |
| B | 0.12 | 58 | 2.1 | Normally active after the injection and 1 day later (male). | IP |
| B | 0.05 | 47 | 1.1 | Normally active after the injection and 1 day later (female). | IP |

TABLE 2-continued

| Solution | Dose (ml) | Weight of Gerbil (g) | Equivalent Dosage of β-carotene (mg/kg) | Toxicity (Activity of Gerbil) | Route of Administration |
|---|---|---|---|---|---|
| C | 0.01 | 51 | 1.8 | Normally active after the injection and 1 and 7 days later. | IP |
| D | 1.1 | 57 | 0 | Normally active after the injection and 24 hours later (male). | IP |
| D | 0.92 | 46 | 0 | Normally active after the injection, and 1 and 7 days later | IP |

EXAMPLE 3

7 week old Sprague Dawley rats (obtained from Ace Animals Inc. of Boyertown, Pa.) were injected intraperitoneally (IP) or intravenously (IV) with solutions A–E of Example 1 at the dosages indicated in Table 3 below to determine their toxicity. Solutions A, C, and E were injected with glass syringes while solutions B and D were injected with plastic syringes. The results are shown in Table 3.

TABLE 3

| Solution | Dose (ml) | Weight of Rat (g) | Equivalent Dosage of β-carotene (mg/kg) | Toxicity (Activity of Rat) | Route of Administration |
|---|---|---|---|---|---|
| A | 0.05 | 243 | 1.9 | Normally active after the injection, and 1 and 7 days later (male). | IV |
| A | 0.05 | 230 | 2 | Normally active after the injection, and 1 and 7 days later (female) | IV |
| B | 0.05 | 256 | 0.2 | Normally active after the injection and 24 hours later. After a second identical injection was given at 24 hours, the animal appeared normally active after the injection and 1 and 6 days after the second injection (male). | IV |
| B | 0.025 | 204 | 0.12 | Normally active after the injection and 24 hours later. After a second identical injection was given at 24 hours, the animal appeared normally active after the injection and 1 and 6 days after the second injection (female). | IV |
| C | 0.1 | 234 | 3.8 | Died within 5 minutes (male) | IV |
| C | 0.05 | 201 | 2.2 | Died within 5 minutes (female). | IV |
| D | 0.3 | 236 | NS | Normally active after the injection, and 1 day later (male).e | IV |
| D | 0.3 | 215 | NS | Normally active after the injection, and 1 and 7 days later. | IV |
| E | 0.1 | 236 | 3.8 | Normally active after the injection and 1 and 6 days later | IP |

EXAMPLE 4

The following experiment was performed three times to determine the absorption of beta-carotene in THF in human hepatocytes.

Materials

Dulbecco's modified Eagle's media (DMEM) was supplemented with amikacin, bovine serum albumin (BSA), fructose, Fungizone, gentamicin, and sodium bicarbonate. The supplemented DMEM is herein referred to as Dulbecco's stock media.

Waymouth media (available as Waymouth 752/1 medium (without phenol red) from Life Technologies, Inc. of Grand Island, N.Y.) was supplemented with amikacin, gentamicin, heptanoic acid, and sodium bicarbonate. The supplemented Waymouth media is herein referred to as the Waymouth Stock Media.

A suspension media was prepared by supplementing DMEM stock media with fetal bovine serum (FBS) and insulin.

A plating media was prepared by supplementing Waymouth stock media with FBS, hydrocortisone, insulin, L-glutamine, and MEM non-essential amino acids.

An incubation media was prepared by supplementing Waymouth stock media with BSA (0.2%), hydrocortisone, insulin, L-glutamine, and MEM non-essential amino acids.

Beta-carotene was dissolved in a solution containing 99.9% (w/w) tetrahydrofuran (THF) with 0.025% (w/w) butylated hydroxytoluene (BHT) to obtain a 2000× (20 mM) stock solution. While the incubation media was rapidly stirred, the stock solution was added to create a final 1× dosing solution containing 10 μM beta-carotene and 0.05% THF.

Amikacin, bovine serum albumin, butylated hydroxytoluene, fetal bovine serum, DMEM powder, fetal bovine serum, fructose, gentamicin sulfate, glycerol, HEPES, heptanoic acid, hydrocortisone 21-hemisuccinate sodium salt, insulin, and MEM non-essential amino acids are available from Sigma Chemical Company of St. Louis, Mo.

Human Hepatocyte Isolation

Hepatocytes were isolated and cryopreserved according to the methods described in Li, A. P., et al., Isolation and culturing of hepatocytes from human liver, *J. Tiss. Culture Methods*, 14:139–146(1992); Li rat and human hepatocytes as multicellular spheroids, *In Vitro Cell. Dev. Biol.*, 28A:673–677 (1992); and Loretz, L. J. et al., Promutagen activation by freshly isolated and cryopreserved rat hepatocytes, *Environ. Mol. Mutag.*, 12(3):335–341. Portions of liver tissue were processed into hepatocytes by collagenase-based digestion of connective tissue, followed by manual and mechanical separation and washing with media. Isolated hepatocytes were counted to determine yield, and viability was measured using Trypan Blue™ exclusion. The viability of the cells was 90%. The cells were resuspended in the plating media described above at a density of $0.7 \times 10^6$ cells/mL.

Human Hepatocyte Incubation

The isolated hepatocytes were transferred to collagen-coated 24-well plates, each well containing a cell density of $3.5 \times 10^5$ viable cells in 0.5 mL of plating media and incubated for 24 hours. The collagen was Vitrogen 100 purified collagen available from Collagen Corporation of Palo Alto, Calif. The cells were incubated at 37° C. in a 95% air and 5% carbon dioxide environment with saturating humidity. After 24 hours, the media were aspirated and replaced with 0.5 mL of the 10 μM beta-carotene dosing solution and the samples were incubated for an additional 24 hours. After this 24 hour incubation period, the dosing solution was replaced with Karnovsky's fixative (available from EM Science of Ft. Washington, Pa.) (0.5 mL/well). The plates were fixed at room temperature for 1 hour. After 1 hour, the fixative was removed and 50% glycerin (0.5 mL/well) was added and the samples were allowed to stand at room temperature for an additional hour. After 1 hour, the glycerin was removed, and the wells were covered with glass coverslips containing one drop of sulfuric acid. The samples were visualized on a light microscope and photographed.

Figure 1:
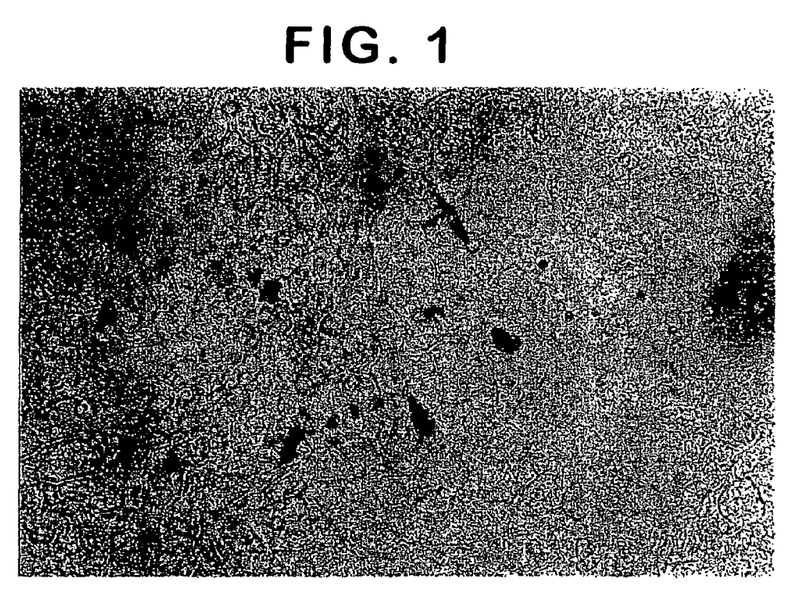
FIGS. 1–3 are photographs at 100 times magnification showing the detection of beta-carotene in cultured human heptacytes incubated with beta-carotene and tetrahydrofuran prepared as in Example 4.
Figure 2:
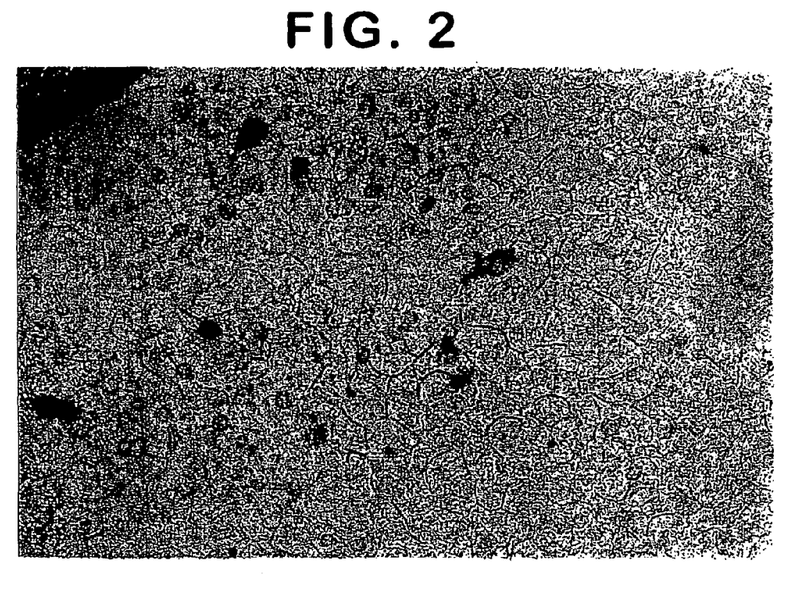
Figure 3:
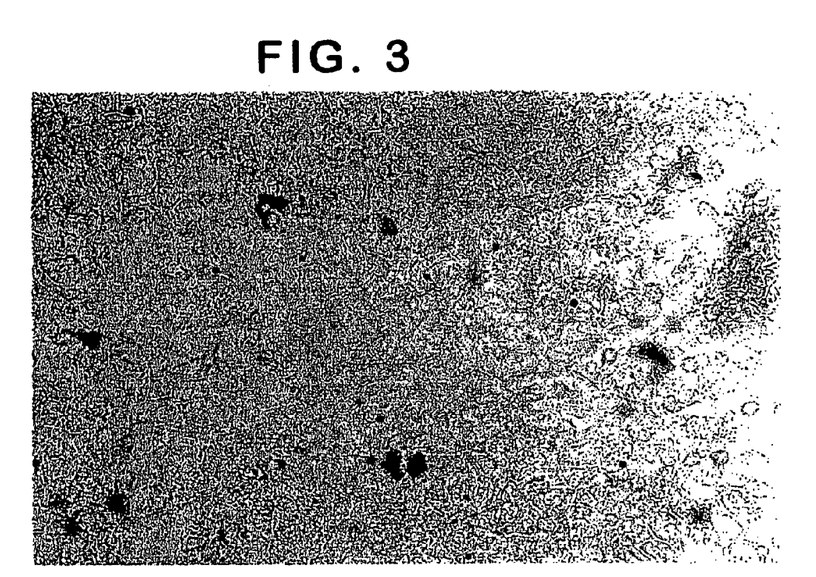

Photographs of three different samples are shown in FIGS. 1–3, respectively.

The presence of beta-carotene in the cells is indicated by the dark regions. (Note that the dark line on the left bottom of FIG. 2 is an artifact.)

EXAMPLE 5

The following experiment was performed three times to determine the amount of beta-carotene in rat hepatocytes dosed with THF without any β-carotene.

Rat Hepatocyte Isolation

Hepatocytes were isolated from fresh liver tissue of a male Sprague-Dawley rat obtained from Harlan-Sprague-Dawley of Indianapolis, Ind., according to the procedure described in Seglen, P. O., Preparation of isolated rat liver cells, *Meth. Cell. Biol.*, 13:29–83(1976). The isolated hepatocytes were then processed as described in Example 4.

Rat Hepatocyte Incubation

The isolated hepatocytes were transferred to collagen-coated 24-well plates, each well containing a cell density of $3.5 \times 10^5$ viable cells in 0.5 mL of plating media. Plating media were removed and replaced with Waymouth media after 24 hours of attachment and incubated at 37° C. After establishing the cultures for 24 hours, the hepatocytes were dosed with THF (as a vehicle control) and incubated as described in Example 4 for 1 hour. The media was removed and replaced with staining fixative (0.5 mL/well). The plates were fixed at room temperature for 1 hour. After 1 hour, the fixative was removed and 50% glycerin (0.5 mnL/well) was added. The plates were allowed to stand at room temperature for an additional hour. After 1 hour, the glycerin was removed and the wells were covered with glass coverslips containing one drop of sulfuric acid. The samples were visualized on a light microscope and photographed.

Figure 4:
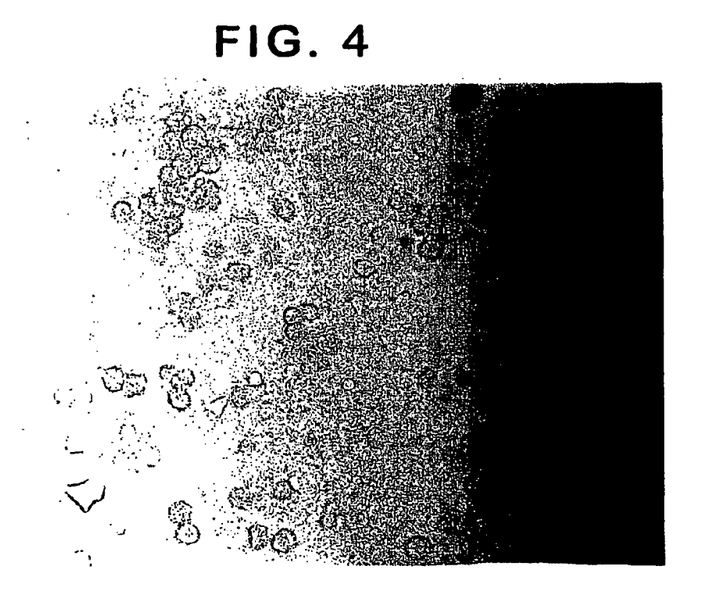
FIGS. 4–6 are photographs at 100 times magnification showing the detection of beta-carotene in cultured rat heptacytes incubated with tetrahydrofuran, but without beta-carotene, prepared as in Example 5.
Figure 5:
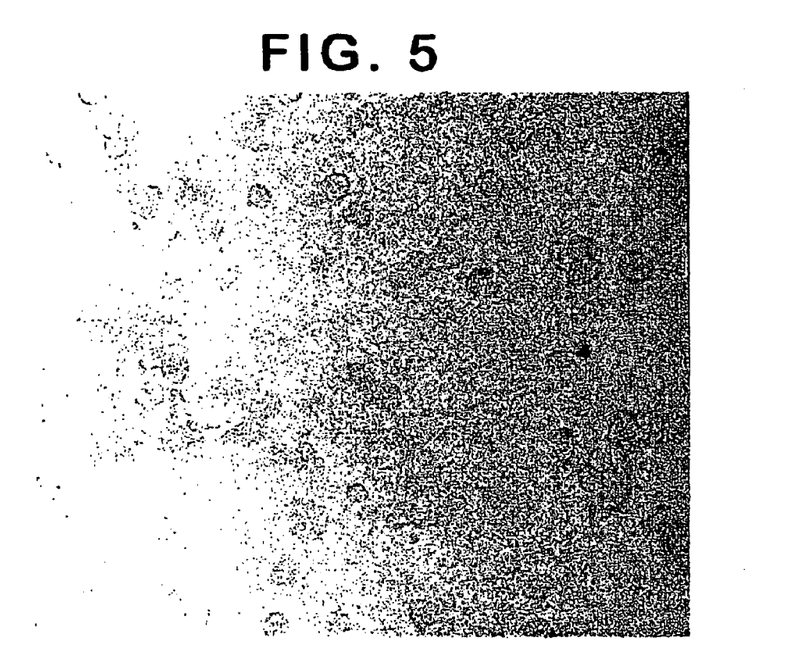
Figure 6:
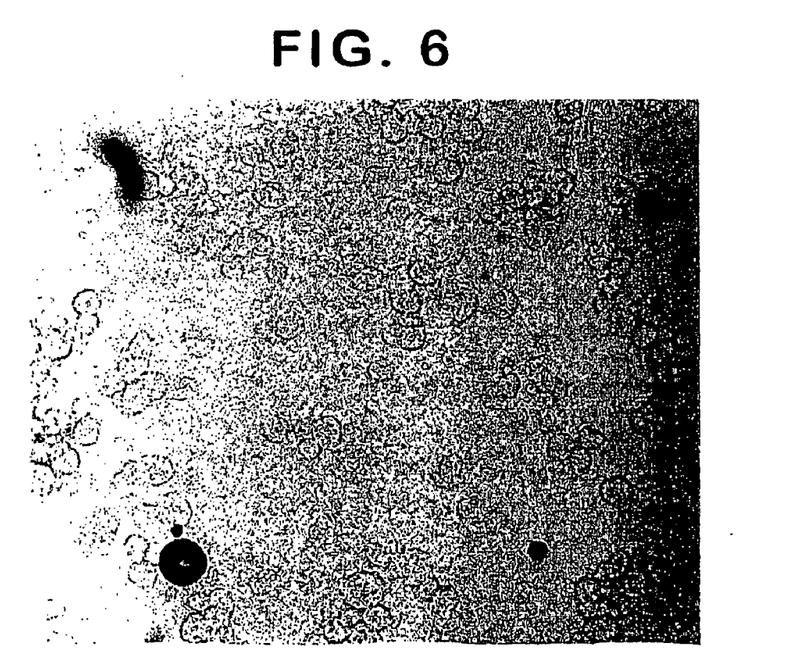

Photographs of three different samples are shown in FIGS. 4-6, respectively.

FIGS. 4–6 reveal no dark regions, showing that beta-carotene was not detected in three different samples incubated only with THF (as a vehicle control). (Note that the dark circles and the dark region in the right corner of FIG. 6 is an artifact.)

EXAMPLE 6

The procedure of Example 5 was repeated without dosing the hepatocytes with THF as a media control.

Figure 7:
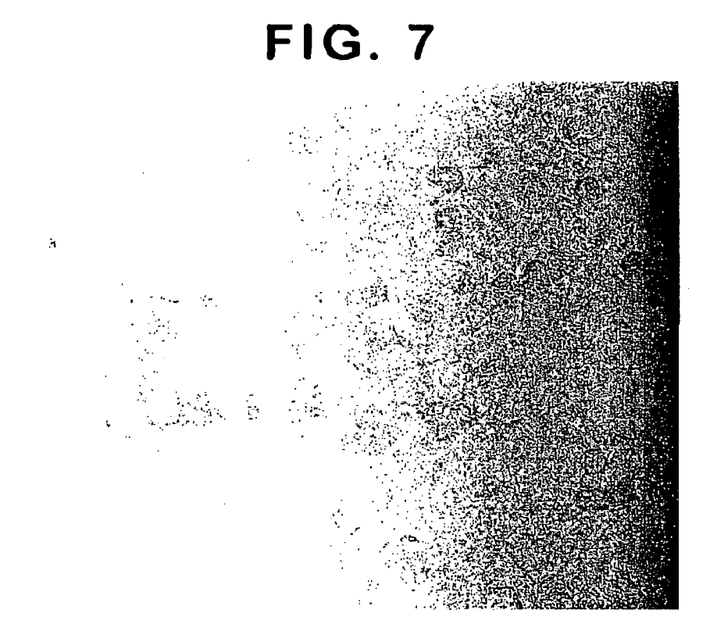
FIGS. 7–9 are photographs at 100 times magnification showing the detection of beta-carotene in cultured rat heptacytes incubated without beta-carotene and tetrahydrofuran, prepared as in Example 6.
Figure 8:
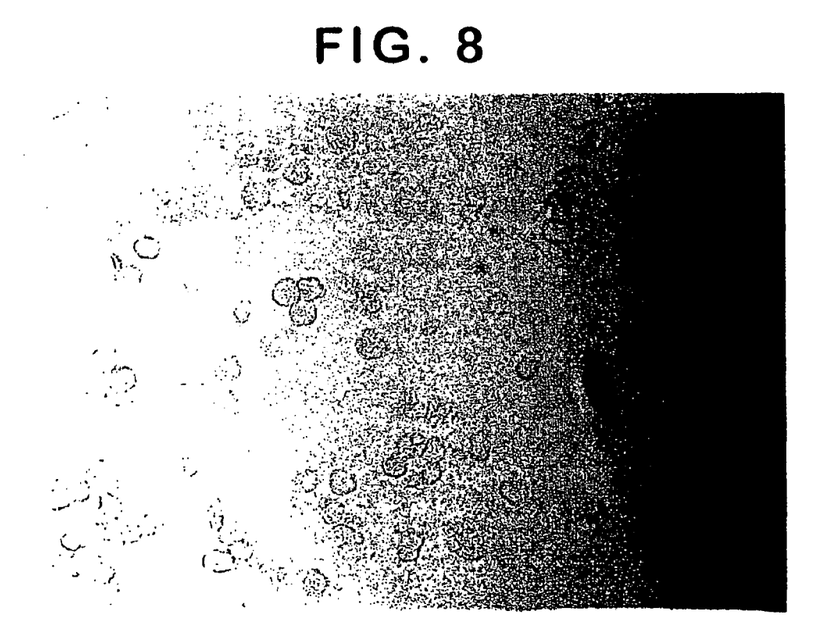
Figure 9:
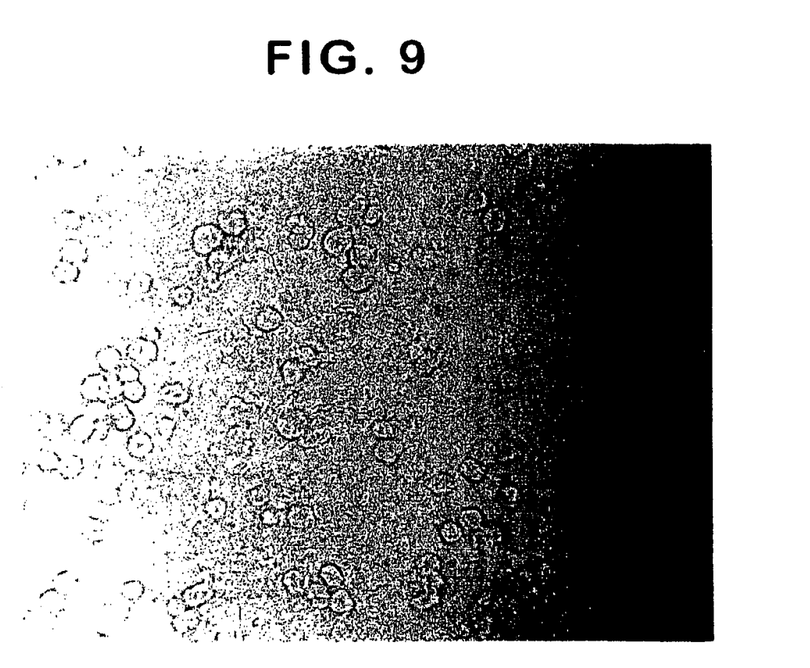

Photographs of three different samples are shown in FIGS. 7–9, respectively.

FIGS. 7–9 reveal no dark regions, showing that beta-carotene was not detected in three different samples incubated only with media (as a media control). (Note that the dark bands in FIGS. 7, 8 and 9, and the dark linear region in FIG. 8 are artifacts.)

EXAMPLE 7

Solution A prepared in Example 1 was splashed on the forearms of a 46 year old Caucasian male weighing 128 pounds. The forearms were washed with soap within 5 minutes of being splashed. After being washed, the orange stain remained. The forearms were washed periodically with soap and detergent over the next 3 days, but failed to remove the stain. No ill effects were noted.

EXAMPLE 8

Treatment of Sepsis with the Compositions of the Present Invention

The rat model for sepsis disclosed in Demetriou et al. (supra) will be employed.

A total of 45 rats will be studied. The rats will be divided randomly into three groups. Group I rats will be untreated controls. Group II will be administered 0.15 mg/kg of beta-carotene in a standard oral formulation. Group III rats will be administered 2 mg/kg of the formulation of the present invention (solution A above, containing 9 mg beta-carotene per ml THF) Beta-carotene administration will be started three days prior to the surgical procedures and continued throughout the postoperative period until the rats die or are sacrificed. All rats will be allocated food and tap water ad libitum. All animals will be anaesthetized with pentobardital sodium (3 mg/100 g intrapeitoneally). The abdomens of the rats will be shaved and cleaned with alcohol. A 2.5 cm midline abdominal incision will be made. The cecum will be delivered through the incision, and a 4-0 silk tie will be placed around the blind segment of the proximal cecum causing complete ischemia but without obstructing the ileocecal junction. The ligated portion of the cecum will be perforated once with an (18-gauge) needle. The abdominal incision will be closed in one layer using a continuous 3-0 silk suture.

It is anticipated that rats receiving the formulation of the present invention will demonstrate improved survival with the prevention of postoperative hypothermia, maintenance of peripheral white blood cell counts and better localization of the intra-abdominal inflammatory process.

EXAMPLE 9

Treatment of Melanoma by Transdifferentiation of Cells into a Benign Phenotype

Experiment: Beta-carotene in tetrahydrofuran (THF) was added to McCoy's 5A modified medium at a concentration of 33 mg/ml with a final concentration of 0.5% THF. This supplemented medium was added to Leighton tubes (containing melanoma cells) after removal of un-supplemented medium and was replaced every 2 days during the 7 day experimental period. At the end of 7 days, the cultures were fixed in methanol and the cover slips were Giemsa stained.

Results: Beta-carotene exerted a dramatic effect on the human melanoma cell cultures. In comparison to control cultures, a large segment of the starting population died during the experimental period. Of the cells that remained, most had triangular morphology and a large nucleus, consistent with neural cells, or were fusiform in shape, consistent with neuroglial or neurolemmal (Schwann) cells.

EXAMPLE 10

Transdifferentiation of Melanoma Cells into Neurons and Neuroglia or Neurolemmal Cells.

Guanosine was added to McCoy's 5A modified medium at a concentration of 3 mg/ml. This supplemented medium was added to Leighton tubes after removal of an non-supplemented medium and was replaced every 2 days for 7 days. Beta-carotene in THF was added to McCoy's 5A modified medium at a concentration of 33 mg/ml with a final concentration of 0.5% THF. This supplemented medium was added to the Leighton tubes after removal of guanosine supplemented medium and was replaced every 2 days for an additional 7 day experimental period. At the end of 14 days, the cultures were fixed in methanol and the cover slips were Giemsa stained.

Results of guanosine treatment followed by beta-carotene treatment of human melanoma cell cultures:

During the 7 day experimental period, guanosine induced phenotypic changes in the overall population such that there were many cells with an increased nuclear to cytoplasmic ratio. There was an increased number of triangular cells consistent with neural phenotypes and cells whose morphology resembled various types of neuroglial or neurilemmal cells. Many cells exhibiting neuronal morphology were observed with two dendritic horns on one end of the cells and a long axonal like projection on the other end. By the end of the 7 day experimental period, these cells were frequent in number and readily observed. Some examples of all phenotypes present in the initial culture were also present after the guanosine treatment, at this dose level. However, subsequent beta-carotene treatment did not cause the extensive cell death as occurred with beta-carotene alone in Example 9 above. Rather, more cells survived, and most of those had a neuronal morphology with a large nucleus, triangular cell body, and processes consistent with dendrites and an axon. Close observation revealed that the cellular processes present on the triangular cells, many times would be directed towards or touching adjacent cells forming what appeared to be a loose network between the cells resembling neural networks.

Significance: It is believed that guanosine caused trans-differentiation of the melanocytic cells to stem cells. This is supported not only by their morphologic changes, but also that the response of these cells to subsequent beta-carotene, in terms of greater survival, suggests that their phenotype changed. Without wishing to be bound by theory, it is believed that beta-carotene further transdifferentiated the stem cells into neurons and neuroglial and neurilemmal cells, and then stabilized these phenotypes so that these cells established a loose network of interconnecting processes resembling neural networks.

EXAMPLE 11

All experimental substances (retinol, retinoic acid, 9-cis retinoic acid, retinal) were from Sigma (St. Louis, Mo.). All experimental substances were provided in sealed ampules.

The solvent, Tetrahydrofuran (stabilized with BHT) was also from Sigma.[1]

[1] In the soluabilization experiments described in Examples 11 and 12 a small amount of yellow material appeared on the bottom of the stopper. In addition, since THF is somewhat volatile, the results are approximate.

Other Materials:

2 ml shell vials from Electron Microscopy Sciences (Fort Washington, Pa.) Hamilton glass syringes (100 microliter, 250 microliter, 500 microliter) were from Fisher Scientific (Pittsburgh, Pa.). Silicone stoppers and other glassware were also from Fisher Scientific.

All of these metabolites/derivatives of beta-carotene were highly soluable in these experiments.

1. Retinoic Acid

All of a retinoic acid ampule (100 mg) was poured into a 2 ml shell vial and stoppered with a silicon stopper. Using a 500 microliter Hamilton syringe, 500 microliters of THF was added to the vial and then shaken by hand.

Using a 100 microliter Hamilton syringe, 25 microliters was added at a time and the vial shaken until soluability was achieved at a total of 575 microliters of THF.

From the present experiment the soluability of retinoic acid is about 174 mg retinoic acid/ml THF, demonstrating high soluability.

2. Retinol a. 25 mg ampule of retinol was poured into a 2 ml shell vial and it soluabilized completely in 250 microliters of THF.

b. 100 mg ampule of retinol was poured into a vial and it soluabilized completely in 0.5 ml of THF.

c. 100 mg ampule of retinol was poured into a vial and it soluabilized completely in 0.1 ml THF.

From these results, the soluability is about 1 gm retinol/ml THF, demonstrating very high soluability.

3. 9-Cis Retinoic Acid.

20 microliters THF from a Hamilton syringe was added to an ampule containing 1 mg of 9-cis retinoic acid. It appeared that complete soluability was achieved. From these results, the soluability is at least 50 mg 9-cis retinoic acid/ml THF, demonstrating high soluability.

4. Retinal

A 100 mg ampule of retinal was emptied into a 2 ml shell vial, and was completely soluabilized with hand shaking in 100 microliters of THF. From these results, the soluability is about 1 gm Retinal/ml THF, demonstrating very high soluability.

Conclusion: All of these metabolites/derivatives of beta-carotene were highly soluable in these quantitative experiments.

EXAMPLE 12

All materials and sources were the same as in Example 11.The only additions were the use of 4.3 ml glass shell vials from Electron Microscopy Sciences, 10 ml glass centrifuge tubes from Fisher, and a 1.25 ml glass Hamilton syringe from Fisher.

These experiments provided further confirmation that these metabolites/derivatives of beta-carotene are highly soluable in THF.

1. Retinoic Acid

All of a retinoic acid (1 gram) ampule was poured into a 10 ml glass centrifuge tube and stoppered with a silicon stopper. 7 ml of THF was added to the tube and then shaken by hand. This was performed twice.

From the present experiment the soluability is about 140 mg Retinoic Acid/ml THF, demonstrating high soluability.

2. Retinol

All of a 1 gram ampule was poured into a 4.3 ml shell vial and stoppered with a silicon stopper. Using a 1.25 ml Hamilton syringe, 1.0 ml of THF was added to the vial and then shaken by hand. It soluabilized completely. From these results, the soluability is about 1 gm Retinol/ml THF, demonstrating very high soluability.

3. 9-Cis Retinoic Acid 10 microliters THF from a Hamilton syringe was added to a ampule containing 1 mg of 9-cis retinoic acid. It appeared that complete soluability was achieved. From these results, the soluability is about 100 mg 9-cis retinoic acid / ml THF, demonstrating high soluability.

4. Retinal

A 500 mg ampule of retinal was emptied into a 2 ml shell vial, and was completely soluabilized with hand shaking in 0.5 ml of THF. From these results, the soluability is about 1 gm Retinal/ml THF, demonstrating high soluability.

Retinol, retinal, and retinoic acid, were each soluabilized in THF as described above and used as follows.

A fingertip amount of each (e.g. retinoic acid, retinol retinal?) was rubbed into the right calf of a 48-year old health professional. Each of the sites had a yellow color as a result. When observed 48 hours later, the sites remained yellow, and there were no signs of toxicity, either topically or systemically.

EXAMPLE 13

Beta carotene, its derivatives (such as retinol, retinoic acid, retinal, retinyl), and other carotenoids when soluabilized in THF, are useful for a variety of purposes.

Without wishing to be bound by theory, it is believed that beta-carotene, and other carotenoids, can be metabolized by virtually any body cell to metabolites including retinol, retinoic acid, retinal, retinyl, other retinoids, and their salts. Thus beta-carotene in THF can be used to cause increased levels of retinoids (and non-retinoid metabolites of beta-carotene) in cells.

Retinol, retinoic acid, retinal, and retinyl can be soluabilized easily and at high concentrations in THF and used to treat retinoid responsive conditions, disorders, and diseases including acne, hair loss (alopecia; genetic or acquired), melanoma (in situ and metastatic), and various benign and malignant neoplasms including carcinomas and sarcomas of the skin and other tissues such as the hematopoietic system.

Saturated solutions of beta-carotene (bc) in THF, retinol in THF, and retinoic acid in THF are prepared. They are then dissolved in sufficient olive oil (Sigma, St. Louis) to give final concentrations of:

beta-carotene 0.5% in vehicle (TIF and olive oil)

retinol 1.0 % in vehicle (THF and olive oil)

retinoic acid 0.5% in vehicle (THF and olive oil)

The shaved mouse model used is that of Shirai, A, Ikeda, J, Kawashima, S, Tamnaoki, T, Kamiya, T. 2001. KF19418A new compound for hair growth promotion in vitro and in vivo mouse models. J. Dermatol. Sci. 25:213–218.

Six mice are in each of the following six groups: saline (negative control), THF 1% in olive oil (vehicle control), minoxidil 5% (Rogaine, Upjohn, Kalamazoo, Michigan) (positive control), beta-carotene in vehicle, retinol in vehicle, and retinoic acid in vehicle.

The dorsa of all mice are shaved. Starting the next day 0.15 ml of each test substance is applied to each animal topically, daily for two weeks. After 2 weeks, all the animals are photographed. They were then sacrificed and the dorsal skin is digitized to count the % area in which hair growth has occurred. The saline control and THF vehicle control show minimal hair growth in this time. The other groups show substantial hair growth.

1. The test substance in THF can be applied with other vehicles such as corn oil or safflower oil, to minimize any potential for irritancy.

2. a. The percentage range of bc in vehicle can be approximately 0.1% to 0.5% as long as the final preparation does not cause irritancy from daily application topically.

b. The percentage range of retinol in vehicle can be approximately 0.1% to 5% as long as the final preparation does not cause irritancy from daily application topically.

c. The percentage range of retinoic acid in vehicle can be approximately 0.1% to 2% as long as the final preparation does not cause irritancy from daily application topically.)

EXAMPLE 14

A human with male pattern baldness applies retinol in THF daily to his thinning vertex. Within 4 months, significant new hair growth is confirmed by hair counts, investigator assessment and patient assessment.

EXAMPLE 15

1. Purpose

To evaluate the tolerability and toxicity of a new preparation of beta-carotene for intraperitoneal (IP) injection in mice.

2. Procedure

A group of BALB/cbjy derived, mice was received from Jackson Laboratories (Bar Harbor, Me.). The animals were singly housed in solid bottom caging. Litter was changed at least once per week. The animal room was temperature controlled and had a 12-hour light/dark cycle. The animals were fed Purina Rodent Chow during the study and filtered tap water was supplied ad libitum.

Following six days of acclimation to the laboratory, 16 healthy mice approximately 5 weeks of age were selected for this study and equally distributed into each of the following dose groups (2 males and 2 females/group):

| Group # | Test/Control Substance | Dose Level (mg/kg) | Dose Volume (ml) |
|---|---|---|---|
| A | beta-carotene in vehicle | 2 | 0.15 |
| B | beta-carotene in vehicle | 6 | 0.45 |
| C | beta-carotene in vehicle | 10 | 0.75 |
| D | Saline | — | 0.75 |

The beta-carotene concentration was prepared once each week by mixing 1 ml of a 9 mg/ml solution of beta-carotene (Sigma Lot #110K2519) in tetrahydrofuran with BHT (Sigma, Lot #C006254B0) into 26 ml olive oil (Sigma, Lot #050K6072). The final concentration of 0.333 mg beta carotene/ml vehicle (THF and olive oil) was made sterile by filtration with a sterile filter (0.45 micron). A 0.9% saline solution was used to dose the control group. Each animal received the appropriate amount of the 0.333 mg/ml solution of beta-carotene in vehicle, as described above, over approximately 15 seconds by intraperitoneal (IP) injection using a 23-gauge needle attached to a 1-cc syringe. After administration, each animal was returned to its designated cage. The IP injections were administered twice a week (Tuesday and Friday) for three weeks.

The animals were observed for mortality, signs of gross toxicity and behavioral changes at least once daily for 21 days. Body weights were recorded prior to the first injection (Day 0) and on Days 7, 14 and 21 or after death. Surviving rats were euthanized via $CO_2$ inhalation on Day 21. Gross necropsies were performed on all decedents and euthanized animals. Tissues and organs of the thoracic and abdominal cavities were examined. The liver from each animal was preserved in 10% neutral buffered formalin for possible future evaluation.

3. Results

One female from Group D (Saline) died on Day 6 of the study. No toxic signs were noted in this animal prior to death. All surviving animals appeared active and healthy throughout the study. Although one female from Group D (Saline) lost body weight between Days 14 and 21 all other animals gained weight over the 21-day observation period. Gross necropsy of the decedent revealed discoloration of the intestines. With the exception of yellow fluid present in the abdominal cavity of most surviving mice, there were no gross abnormalities noted for any euthanized animals necropsied at the conclusion of the 21-day observation period.

4. Conclusion

This formulation of beta-carotene in THF (mixed into olive oil) and injected IP biweekly for three weeks into 5 week old BALB/cbjy mice at doses of approximately 2 mg/kg and 10 mg/kg was well tolerated and without gross toxicity.

All references cited herein are incorporated by reference in their entirety.

What I claim is:

1. A systemic formulation comprising:
   (a) an agent selected from beta-carotene, retinol, retinal, 9-cis retinoic acid, retinoic acid and retinyl; and
   (b) tetrahydrofuran, and polyethylene glycol as a solubilizer.

2. The systemic formulation of claim 1, wherein said agent is beta-carotene.

3. The systemic formulation of claim 2, wherein the formulation comprises a therapeutically effective amount of beta-carotene.

4. The systemic formulation of claim 2, wherein the formulation comprises from about 0.1 to about 9.3 mg of beta-carotene per ml of tetrahydrofuran.

5. The systemic formulation of claim 4, wherein the formulation comprises from about 1 to about 6 mg of beta-carotene per ml of tetrahydrofuran.

6. The systemic formulation of claim 2, wherein the polyethylene glycol has a molecular weight ranging from about 200 to about 600 daltons.

7. The systemic formulation of claim 2, wherein the polyethylene glycol is PEG 200.

8. The systemic formulation of claim 2, wherein the formulation comprises from about 0.02 to about 2 mg of beta-carotene per ml of polyethylene glycol.

9. The systemic formulation of claim 8, wherein the formulation comprises from about 0.1 to about 1 mg of beta-carotene per ml of polyethylene glycol.

10. The systemic formulation of claim 9, wherein the weight ratio of tetrahydrofuran to polyethylene glycol ranges from about 90:10 to about 99.5:0.5.

11. The systemic formulation of claim 10, wherein the weight ratio of tetrahydrofuran to polyethylene glycol ranges from about 90:10 to about 99:1.

12. The systemic formulation of claim 11, wherein the weight ratio of tetrahydrofuran to polyethylene glycol is about 97:3.

13. The systemic formulation of claim 1, wherein the formulation is a liquid.

14. The systemic formulation of claim 13, further comprising:
   (c) an excipient;
   (d) a stabilizer;
   (e) a buffer;
   (f) a diluent;
   (g) a suspending agent;
   (h) a preservative;
   (i) a colorant;
   (j) a dosing vehicle; or
   (k) any combination of any of the foregoing.

15. The systemic formulation of claim 14, wherein the suspending agent is carboxymethyl cellulose.

16. The systemic formulation of claim 14, wherein the formulation comprises from about 5 to about 95% by weight of suspending agent, based upon 100% total weight of formulation.

17. The systemic formulation of claim 14, wherein the preservative is butylated hydroxytoluene.

18. The systemic formulation of claim 14, wherein the formulation comprises from about 0.01 to about 5% by weight of preservative, based upon 100% total weight of formulation.

19. The systemic formulation of claim 14, wherein the dosing vehicle is an oil.

20. The systemic formulation of claim 19, wherein the dosing vehicle is corn oil.

21. The systemic formulation of claim 14, wherein the formulation comprises from about 5 to about 95% by weight of dosing vehicle, based upon 100% total weight of formulation.

22. The systemic formulation of claim 1, wherein the formulation is a solid or a gel.

23. The systemic formulation of claim 22, further comprising:
   (c) an excipient;
   (d) a diluent;
   (e) a stabilizer;
   (f) a disintegrant;
   (g) a lubricant;
   (h) a plasticizer;
   (i) a colorant;
   (j) a preservative;
   (k) a dosing vehicle; or
   (l) any combination of any of the foregoing.

24. A method for administering an agent selected from beta-carotene and derivatives thereof to an animal in need thereof, the method comprising administering to the animal a composition comprising beta-carotene and derivatives thereof and a combination of tetrahydrofuran and polyethylene glycol as a stablizer.

25. The method of claim 24, wherein the composition is administered parenterally.

26. The method of claim 24, wherein the composition is administered orally.

27. The method of claim 24, wherein the composition is administered topically.

28. The method of claim 24, wherein the composition comprises from about 0.1 to about 9.3 mg of beta-carotene and derivatives thereof per ml of tetrahydrofuran.

29. The method of claim 24, wherein the composition comprises from about 0.02 to about 2 mg of beta-carotene and derivatives thereof per ml of polyethylene glycol.

30. The method of claim 24, wherein a therapeutically effective amount of the composition is administered.

31. The method of claim 24, wherein the animal is a mammal.

32. The method of claim 31, wherein from about 0.01 to about 1,000 mg of the composition is administered per kg of animal weight.

33. A method for treating a disorder selected from sepsis, age related macular degeneration, melanoma, acne, alopecia and abnormal immunological and serological indicies in an animal comprising administering to the animal a therapeutically effective amount of a composition comprising beta-carotene and derivatives thereof and combination of tetrahydrofuran and polyethylene glycol as a stabilizer.

34. A method for treating sepsis in an animal comprising administering to an animal in need of such treatment an amount effective to treat sepsis of the formulation of claim 1.

* * * * *

UNITED STATES PATENT AND TRADEMARK OFFICE
CERTIFICATE OF CORRECTION

PATENT NO. : 6,878,747 B2 Page 1 of 1
APPLICATION NO. : 10/466825
DATED : April 12, 2005
INVENTOR(S) : Steven Baranowitz It is certified that error appears in the above-identified patent and that said Letters Patent is hereby corrected as shown below:

On the Title Page, Item (60)

In the Related U.S. Application Data please insert:

-- Application is a 371 of PCT/US02/02465 1/28/05 --.

Signed and Sealed this

Seventeenth Day of June, 2008

JON W. DUDAS
*Director of the United States Patent and Trademark Office*